(12) United States Patent
Kalloniatis et al.

(10) Patent No.: US 10,390,695 B2
(45) Date of Patent: Aug. 27, 2019

(54) METHODS AND SYSTEMS FOR DIAGNOSIS OF OCULAR DISEASE

(71) Applicant: NewSouth Innovations Pty Limited

(72) Inventors: Michael Kalloniatis, Randwick (AU); Sieu Khuu, Padstow (AU); Noha Al Saleem, Kingsford (AU)

(73) Assignee: Newsouth Innovations Pty Limited, New South Wales (AU)

( * ) Notice: Subject to any disclaimer, the term of this patent is extended or adjusted under 35 U.S.C. 154(b) by 364 days.

(21) Appl. No.: 14/652,646

(22) PCT Filed: Dec. 5, 2013

(86) PCT No.: PCT/AU2013/001431
§ 371 (c)(1),
(2) Date: Jun. 16, 2015

(87) PCT Pub. No.: WO2014/094035
PCT Pub. Date: Jun. 26, 2014

(65) Prior Publication Data
US 2015/0313457 A1    Nov. 5, 2015

(30) Foreign Application Priority Data
Dec. 20, 2012  (AU) ............................... 2012905587

(51) Int. Cl.
*A61B 3/00*   (2006.01)
*A61B 5/00*   (2006.01)
(Continued)

(52) U.S. Cl.
CPC ............ *A61B 3/024* (2013.01); *A61B 3/0025* (2013.01); *A61B 3/0041* (2013.01); *A61B 3/032* (2013.01);
(Continued)

(58) Field of Classification Search
CPC ..... A61B 3/024; A61B 3/0025; A61B 3/0041; A61B 3/032
See application file for complete search history.

(56) References Cited

U.S. PATENT DOCUMENTS 5,461,435 A    10/1995  Rootzen et al.
5,717,481 A *  2/1998  Obata .................... A61B 3/024
                                                351/224
(Continued)

FOREIGN PATENT DOCUMENTS

WO         9424925       11/1994
WO      2008013907 A2     1/2008
WO      2008013907 A3     1/2008

OTHER PUBLICATIONS

IPS Standards and Guidelines 2010: http://webeye.ophth.uiowa.edu/ips/GEN-INFO/standards/standards2010/IPS-Standards2010.pdf.*

(Continued)

*Primary Examiner* — Devin B Henson
(74) *Attorney, Agent, or Firm* — Hanley, Flight and Zimmerman, LLC

(57) ABSTRACT

An aspect of the present invention provides a method for early detection of ocular disease such as glaucoma in a subject. The method comprises the steps of: successively applying a plurality of test stimuli at different eccentricities to the subject's retina, wherein each of the test stimuli is adjusted for differences in spatial or temporal summation resulting from application of the test stimuli; determining visual field capability loss of the subject in response to each of the plurality of test stimuli; and diagnosing ocular disease in the subject if the subject's visual field capability loss in response to each of the test stimuli is substantially equal.

15 Claims, 9 Drawing Sheets

(51) Int. Cl.
*A61B 3/024* (2006.01)
*A61B 3/032* (2006.01)

(52) U.S. Cl.
CPC .... *A61B 5/7282* (2013.01); *A61B 2560/0475* (2013.01)

(56) References Cited

U.S. PATENT DOCUMENTS

| | | | |
|---|---|---|---|
| 2003/0036907 A1 | 2/2003 | Stewart et al. | |
| 2008/0024724 A1 | 1/2008 | Todd | |
| 2008/0024725 A1 | 1/2008 | Todd | |
| 2008/0043201 A1 | 2/2008 | Todd | |
| 2012/0075586 A1* | 3/2012 | Kirschen | A61B 3/032 351/239 |
| 2012/0127430 A1* | 5/2012 | Rotenstreich | A61B 3/024 351/210 |

OTHER PUBLICATIONS

Wyatt et al., "Variability of visual field measurements is correlated with the gradient of visual sensitivity", Vision Research, vol. 47, Issue 7, Mar. 2007, pp. 925-936.*

International Search Report, issued by the International Searching Authority in connection with International patent application No. PCT/AU2013/001431, dated Mar. 11, 2014, 2 pages.

Anderson R. S.,"The psychophysics of glaucoma: Improving the structure/function relationship," Progress in Retinal and Eye Research, vol. 25, 2006, 19 pages.

Bengtsson, B. et al., "A new generation of algorithms for computerized threshold perimetry, SITA," Acta Ophthalmologica Scandinavica. 1997; vol. 75, 8 pages.

Fellman, R. L. et al., "Clinical importance of spatial summation in glaucoma," Proceedings of the 8th International Perimetric Society Meeting, 1989, 12 pages.

Redmond, T. et al., "Sensitivity Loss in Early Glaucoma Can Be Mapped to an Enlargement of the Area of Complete Spatial Summation," Investigative Ophthalmology & Visual Science, Dec. 2010, vol. 51, No. 12, 9 pages.

Extended European Search Report, issued by the European Patent Office in connection with European Patent Application No. 13865419.9, dated Jul. 19, 2016, 6 pages.

Communication Pursuant to Article 94(3) EPC, issued by the European Patent Office in connection with European Patent Application No. 13865419.9, dated Aug. 8, 2017, 3 pages.

European Patent Office, "Communication pursuant Article 94(2) EPC," issued in connection with European patent application No. 13865419.9 , dated Feb. 27, 2018, 4 pages.

* cited by examiner

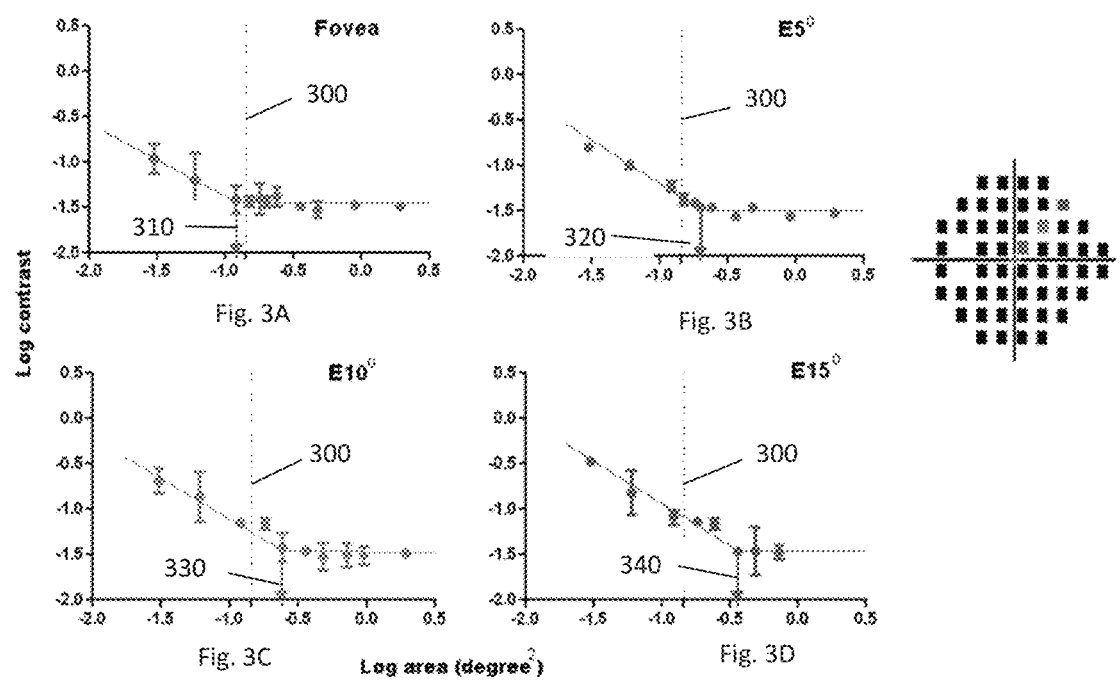

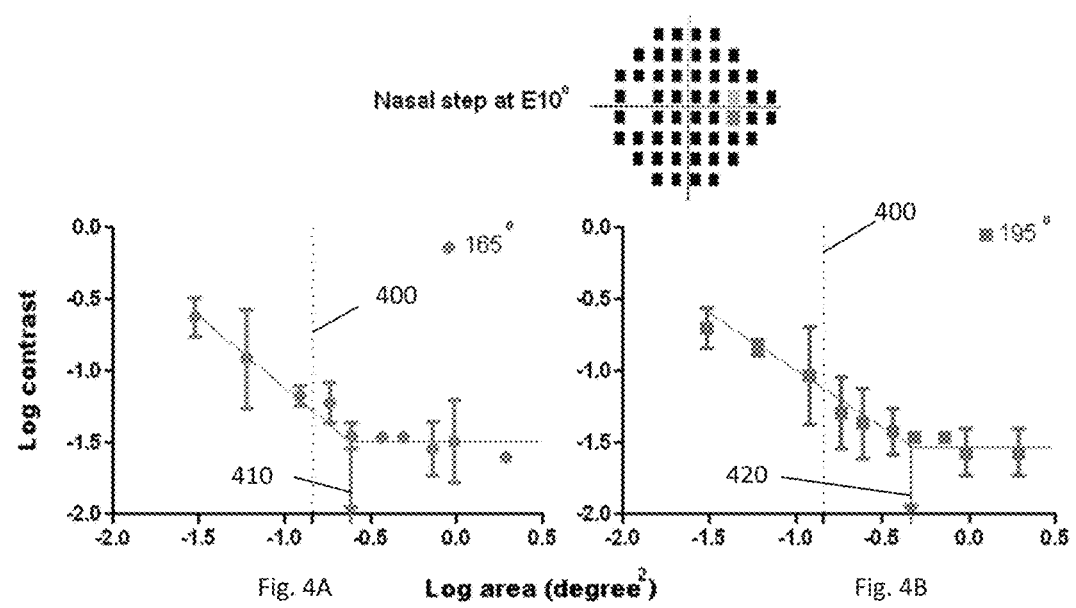

METHODS AND SYSTEMS FOR DIAGNOSIS OF OCULAR DISEASE

RELATED APPLICATIONS

This patent is a continuation of International Patent Application Serial No. PCT/AU2013/001431, filed Dec. 5, 2013, which claims priority to Australian Patent Application 2012905587, filed on Dec. 20, 2012, both of which are hereby incorporated herein by reference in their entireties.

TECHNICAL FIELD

The present invention relates to automated visual field testing for diagnosis of ocular disease and more particularly for early detection of ocular disease such as glaucoma.

BACKGROUND

Glaucoma is an optic neuropathy that causes distinctive morphological changes of the optic nerve head (ONH) and retinal nerve fibre layer (RNFL) associated with distinctive visual field changes. It is one of the leading causes of world blindness causing asymptomatic progressive permanent vision loss. Patients generally remain asymptomatic until large irreversible visual field defects develop. Typically, 25-35% of the RNFL must be damaged before a visual field effect can be detected. As a consequence, early detection is a key requirement so that medical or surgical intervention can be initiated to prevent irreversible vision loss.

Accordingly, a need exists for improved methods and systems for early detection and/or diagnosis of glaucoma and other ocular diseases.

SUMMARY

An aspect of the present invention provides a method for early detection of ocular disease in a subject. The method comprises the steps of: successively applying a plurality of test stimuli at different eccentricities to the subject's retina, wherein each of the test stimuli is adjusted for differences in spatial or temporal summation resulting from application of the test stimuli; determining visual field capability loss of the subject in response to each of the plurality of test stimuli; and diagnosing ocular disease in the subject if the subject's visual field capability loss in response to each of the test stimuli is substantially equal.

Another aspect of the present invention provides a visual field analysis system comprising: at least one processor; memory coupled to the at least one processor for storing program instructions and data; a visual stimuli generator coupled to the at least one processor for generating and applying visual stimuli to a subject's retina; a visual analyzer coupled to the at least one processor for determining visual field capability loss in the subject; and a visual display coupled to the at least one processor for outputting information. The at least one processor is programmed to: apply, using the visual stimuli generator, a plurality of different test stimuli at different eccentricities to a subject's retina, wherein each of the test stimuli is adjusted for differences in spatial or temporal summation resulting from application of the test stimuli; identify, using the visual analyzer, visual field capability loss of the subject in response to each of the plurality of test stimuli; determine whether the visual field capability loss in response to each of the test stimuli is substantially equal; and output, using the display, a result of the determination.

Another aspect of the present invention provides a method for early detection of ocular disease in a subject. The method comprises the steps of: successively applying a plurality of test stimuli at different eccentricities to the subject's retina, wherein one or more of the test stimuli fall within Ricco's law and one or more of the test stimuli fall outside Ricco's law; comparing threshold response of the subject to the test stimuli at various eccentricities; and determining visual field capability loss of the subject due to ocular disease based on the threshold response comparison.

Another aspect of the present invention provides a visual field analysis system comprising: at least one processor; memory coupled to the at least one processor for storing program instructions and data; a visual stimuli generator coupled to the at least one processor for generating and applying visual stimuli to a subject's retina; a visual analyzer coupled to the at least one processor for determining visual field capability loss in the subject; and a visual display coupled to the at least one processor for outputting information. The at least one processor is programmed to: deliver, using the visual stimulator, a plurality of different test stimuli at different eccentricities to a subject's retina, wherein one or more of the test stimuli fall within Ricco's law and one or more of the test stimuli fall outside Ricco's law; compare, using the visual analyzer, threshold response of the subject to the test stimuli at various eccentricities; determine visual field capability loss of the subject due to ocular disease based on the threshold response comparison; and output, using the video display, a result of the determination.

BRIEF DESCRIPTION OF THE DRAWINGS

Embodiments are described hereinafter, by way of example only, with reference to the accompanying drawings in which:

FIGS. 3A-3D shows the relation between various test stimuli and critical area at various eccentricities on the same meridian on a log-log plot of threshold as a function of area;

FIGS. 4A and 4B shows the relation between various test stimuli and critical area at different locations (nasal steps) for the same eccentricity on a log-log plot of threshold as a function of area;

The graphical representations of threshold/sensitivity as a function of test stimulus size and duration in the above-mentioned figures are relatively simplistic two-line fit plots (i.e., comprising slopes of −1 and 0). However, thresholds at larger test stimuli (i.e., outside of Ricco's and Bloch's laws) do not generally follow a slope of zero on account of being insufficiently large to guarantee complete spatial or temporal summation. A three-line fit will therefore provide a more accurate representation, with a portion of the curve fit having a slope of −0.5.

The use of common reference designators in different figures is intended to convey that the items or steps referred to in the different figures are identical or substantially similar.

DETAILED DESCRIPTION

The methods and systems described herein relate to automated visual field testing for the detection and/or diagnosis of ocular diseases. The methods and systems are described with specific reference to early detection of glaucoma, however, it is not intended that the present invention be limited to this specific application as the principles of the present invention have general applicability to the diagnosis and/or detection of other ocular diseases.

The average human retina is approximately 0.5 mm thick and has a diameter of 30-40 mm. The central retina comprises the macula and fovea (approximately 6 mm). Beyond the central retina is the peripheral retina, which extends to 21 mm and ends at the ora-serrata. The human retina comprises different kinds of cells on different layers. The main cells of interest are the ganglion cells, which send stimuli from photoreceptors through the optic nerve to the central visual pathways. Ganglion cells are connected to the photoreceptors via bipolar cells. This connection differs between the central retina and the periphery.

Figure 1A:
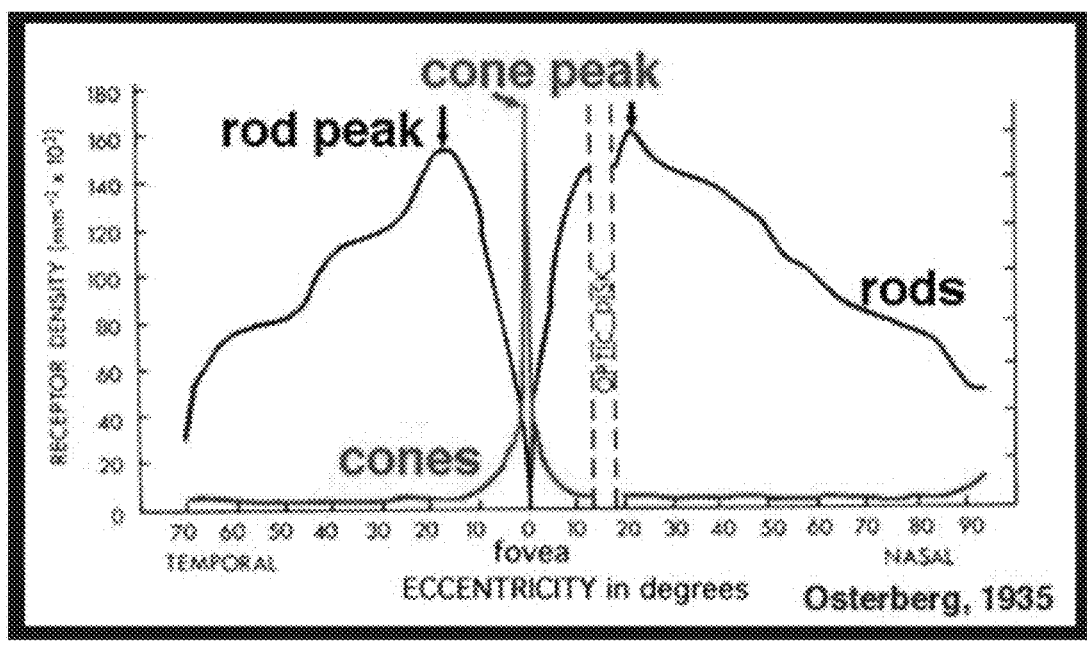
FIG. 1A is a graphical representation of cone and rod retinal distribution as a function of eccentricity.
Figure 1B:
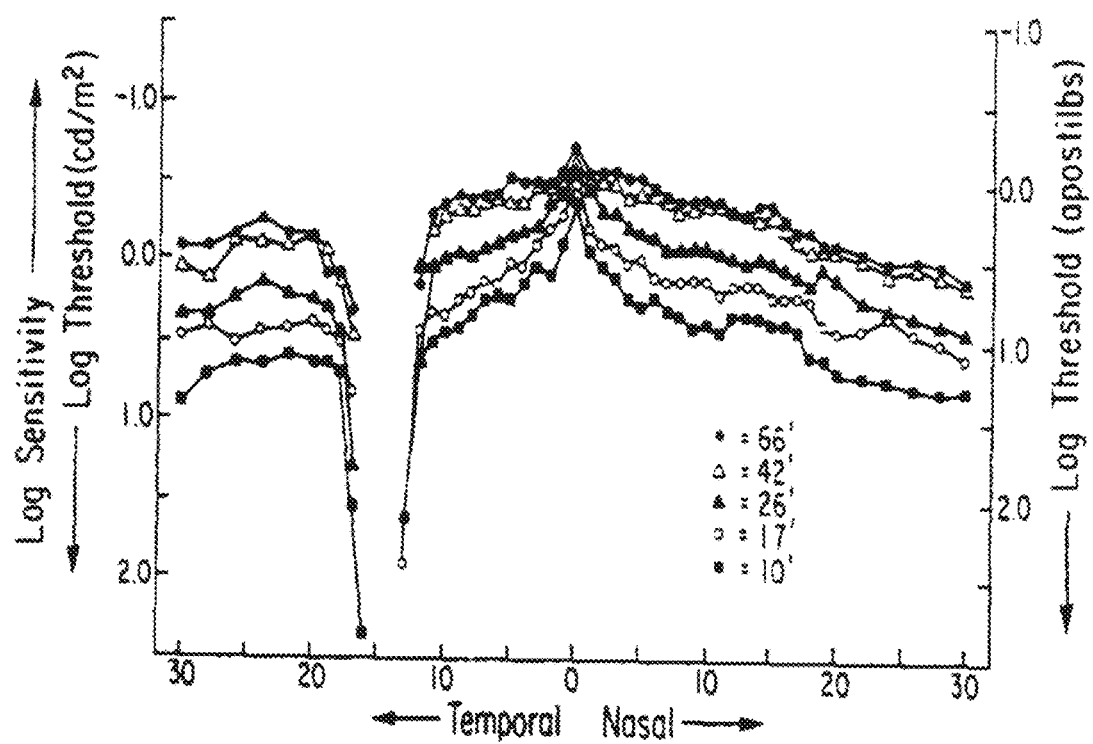
FIG. 1B is a graphical representation of visual sensitivity as a function of eccentricity for cone function using different size stimuli.

Changes in sensitivity between the fovea and eccentric locations of the retina are affected by the numbers of 'cone' and 'rod' detectors and their associated circuitry. Under photopic conditions, where thresholds are measured to establish sensitivity of visual field, cone photoreceptors mediate detection. The change in visual sensitivity as a function of eccentricity is dependent on cone density and circuitry, as shown in FIGS. 1A and 1B, hereinafter. FIG. 1A shows receptor density as a function of eccentricity and FIG. 1B shows sensitivity and threshold (log scales) as a function of eccentricity for different test size stimuli under photopic conditions.

In the fovea, which is dominated by a massive number of closely spaced cones, the connection is almost one to one. Away from the macula, however, the retina becomes dominated by rods with fewer cones, and cone pathway connections are also reduced. The modification in cone circuitry is reflected by a change of one-to-one (photoreceptor-to-ganglion cell) to many (10-20 photoreceptors-to-one ganglion cell). This difference is a reason for differing central and peripheral retinal thickness and vision sensitivity under photopic conditions. In other words, this difference explains the fact that critical area varies with eccentricity because receptive field size varies with eccentricity and resolution capability is limited by the size of spatial summation.

Changes in sensitivity from the fovea to eccentric locations are described by certain relevant psychophysical laws. Ricco's law (of spatial summation) and Bloch's law (of temporal summation) relate to different perceptual attributes, which explain the threshold response of size and duration of exposure to stimuli, respectively. These two laws are similar in that if the size or the duration of a stimulus is increasing, a reciprocal relationship with luminance must be considered to have a constant value of threshold, which is called critical area (Ac) or critical time (tc). Ac and tc vary for the rod (scotopic) and cone (photopic) visual system. The description here relates to photopic conditions—reflecting the light levels used to measure sensitivity in standard visual fields investigations.

Figure 2A:
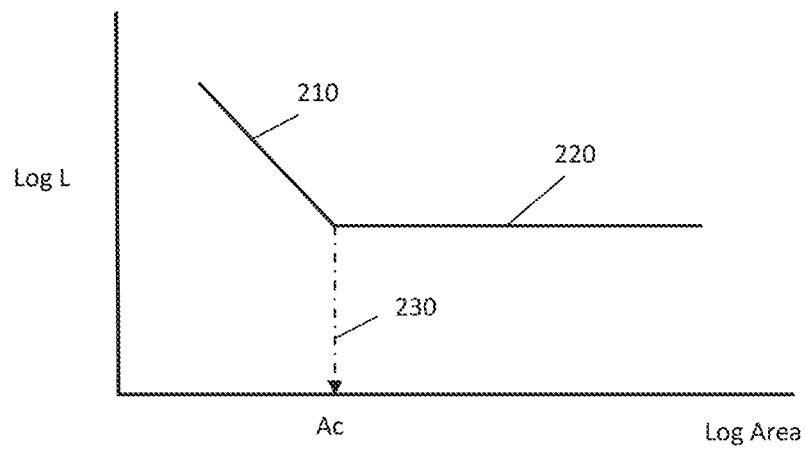
FIG. 2A is a graphical representation of Ricco's law on a log-log plot of threshold as a function of test stimulus area.

FIG. 2A shows a graphical representation of Ricco's law. The graph of FIG. 2A comprises a log-log plot of threshold as a function of test stimulus area. Ricco's law applies while complete spatial summation 210 occurs (i.e., when the slope=−1). The Critical Area (Ac) corresponds to where the threshold has been reduced to its minimum 230. In this simplistic diagram, incomplete spatial summation (Piper's law, slope=−0.5) is not shown. Determining the transition between the regions of Ricco's law 210, Piper's law (not shown), and the linear component 220 (slope=0), is critical to determine test size to ensure the stimulus is within Ricco's law.

Figure 2B:
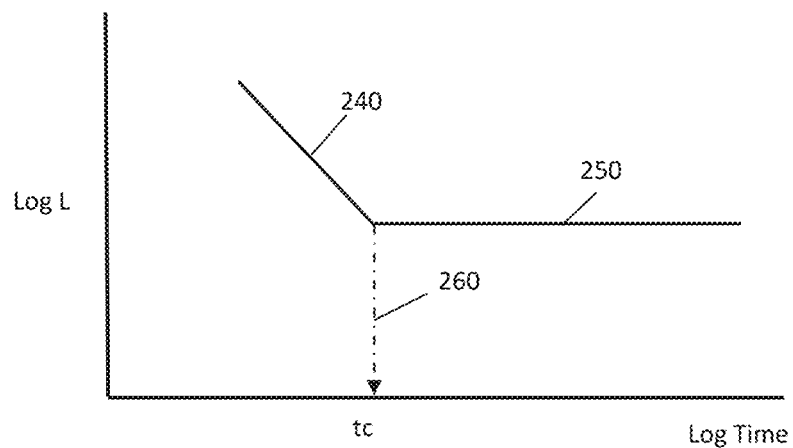
FIG. 2B is a graphical representation of Bloch's law on a log-log plot of threshold as a function of test stimulus duration.

FIG. 2B shows a graphical representation of Bloch's law. The graph of FIG. 2B comprises a log-log plot of threshold as a function of test stimulus duration. Bloch's law applies while complete temporal summation 240 occurs (i.e., when the slope=−1). The Critical Duration (tc) corresponds to where the threshold has been reduced to its minimum 260. In this simplistic diagram, incomplete temporal summation (slope=−0.5) is not shown. Determining the transition between the regions of Bloch's law 240, incomplete temporal summation (not shown), and the linear component 250 (slope=0), is critical to determine test duration to ensure the stimulus is within Bloch's law.

Different retinal positions have different critical areas. In particular, the critical area described by Ricco's law and the critical duration described by Bloch's law both vary with eccentricity. However, critical area at different retinal eccentricities has not been well explored to date. Bloch's law has been characterized for differing eccentricities and the maximum duration has been found to be 100 ms away from the fovea (for photopic vision). Accordingly, any stimulus durations that exceed 100 ms will be under complete temporal summation for any eccentricity.

Various existing techniques correlate function with structure for the evaluation of ocular health. Two such tests include:

Standard Automated Perimetry (SAP) for testing vision sensitivity; and

Optical Coherence Tomography (OCT) for measuring retinal nerve fiber layer thickness anywhere in the retina.

The visual field (white-on-white) Standard Automated Perimetry (SAP) test is one of the gold standard tests for the diagnosis and progression of glaucoma. However, the SAP test is considered to be late in predicting functional loss compared with structural damage with poor overall correlation between function (visual field results) and structure (anatomy). The reason for this discrepancy is the use of test stimuli that are within or outside Ricco's law at the different retinal eccentricities. The belief that structural damage occurs ahead of functional loss is a common misconception.

The present inventors realized that a different retinal stimulus is needed for early detection of ocular disease such as glaucomatous damage. Put differently, the spatial and temporal measurements used in the SAP test are not the ideal parameters for identifying early defects and providing a good measure to match with anatomical changes for detection of the early stages of glaucoma and other ocular diseases.

Table 1, hereinafter, shows standard size test targets (known as the Goldmann test targets), which are available on typical automated visual field analyzers analysers such as the Humphrey Visual Field Analyzer (HVFA).

TABLE 1

Goldmann test targets (I through V available on the HVFA)

| TEST | mm(diam) | mm2 | diam (deg) | Area (deg2) | log Area |
|---|---|---|---|---|---|
| 0 | 0.28 | ¹⁄₁₆th | 0.05375 | 0.00227 | −2.64 |
| I | 0.56 | ¼th | 0.1075 | 0.00908 | −2.04 |
| II | 1.13 | 1 | 0.215 | 0.0363 | −1.44 |
| III | 2.26 | 4 | 0.43 | 0.145 | −0.838 |
| IV | 4.51 | 16 | 0.86 | 0.581 | −0.236 |
| V | 9.03 | 64 | 1.72 | 2.32 | 0.366 |

The Humphrey Visual Field Analyzer (HVFA) standard III target is 0.43 degrees in diameter (area=0.145 degree$^2$) and is presented for a 200 millisecond duration for all eccentricities. Such a presentation strategy does not take into account differences in critical area and duration for the human visual system for different eccentricities.

Table 2, hereinafter, shows a comparison between retinal measurement of critical area and duration and test size III of the HVFA.

TABLE 2

| | Visual psychophysics | | HVFA*** | |
|---|---|---|---|---|
| Eccentricity | Critical area (degree$^2$)* | Critical duration calculated from critical flicker frequency (CFF) (millisecond)** | Stimulus size III = 0.43° diameter = (degree$^2$) | Stimulus duration (millisecond) |
| 5° | 0.05 | 29 | 0.145 | 200 |
| 10° | 0.08 | n/a | 0.145 | 200 |
| 15° | 0.13 | 56 | 0.145 | 200 |
| 20° | 0.18 | n/a | 0.145 | 200 |

*(Sloan, 1961)
**(Kolb et al., 2005)
***From: (Codicil, 1990) (Zeiss, 2010)

If a comparison is made between the stimulus size of the HVFA and known critical areas levels, the HVFA stimulus is larger than the critical area for 5, 10 and 15 degrees of eccentricity, but falls within critical area for larger eccentricities (see Table 2, above). Furthermore, the test stimulus duration (200 milliseconds) always places the test outside the critical duration for all eccentricities (see Table 2, above).

The HFVA presents one stimulus size at all eccentricities. Given that the two approaches, static versus kinetic perimetry employ different strategies, the use of one test size may result in probing of different mechanisms at different retinal eccentricities. Loss of detectors when the system is operating within total spatial summation may lead to different sensitivity measures compared to the use of stimuli that probe the system when it is operating under incomplete spatial summation conditions. Thus, stimuli falling within Ricco's law (i.e., stimuli smaller than the critical area) will be relatively more sensitive to detect a loss of visual function.

This accords firstly with the present inventors' observation, from results of work performed by Harwerth et al. in a paper entitled "Scaling the structure-function relationship for clinical perimetry", published in ActaOphthalmol Scand. 2005 83(4):448-55, that structure function correlation performed at different eccentricities displays a significantly different slope for different eccentricities. Such a relationship would be experienced if functional measures were not reflecting visual mechanisms operating under the same conditions.

Secondly, Redmond et al., in a paper entitled "*Sensitivity Loss in Early Glaucoma Can be Mapped to and Enlargement of the Area of Complete Spatial Summation*", Investigative Ophthalmology & Visual Science 51(12): 6540-6548, showed a significantly larger loss in glaucoma subjects for stimuli within Ricco's critical area compared to larger stimuli test. The present inventors concluded, from the results of Redmond et al., that the use of stimuli under incomplete summation (i.e., smaller stimuli) will lead to larger threshold elevations in the early stages of glaucoma. Given the available data, the present inventors predicted that the seminal sign of early glaucoma, the nasal step, should show different Ac values for the same eccentricity (at ~10-25 degrees temporally) just above and just below the horizontal meridian.

The present inventors conducted experiments to determine critical area as a function of eccentricity and different orientations in subjects having normal visual field capability. The subjects were subjected to visual psychophysical testing and the collected data was processed or analyzed using a non-parametric bootstrap paradigm to determine various parameters, including critical area (Ac). The results are presented hereinafter with reference to FIGS. 3A-3D and FIGS. 4A-4B.

FIGS. 3A-3D show the relation between various test stimuli and critical area at various eccentricities on the same meridian. In each of FIGS. 3A-3D, the vertical dashed line 300 represents the area tested by the Goldmann standard size III. The test size III is clearly not compatible for all eccentricities as it lies within the linear region for the foveal data and just within Ricco's law at E15. The vertical arrow 310 in FIG. 3A identifies the critical area when the stimulus is applied to the fovea. The vertical arrow 320 in FIG. 3B identifies the critical area when the stimulus is applied at an eccentricity of 5°. The vertical arrow 330 in FIG. 3C identifies the critical area when the stimulus is applied at an eccentricity of 10°. The vertical arrow 340 in FIG. 3D identifies the critical area when the stimulus is applied at an eccentricity of 15°.

As shown in FIGS. 3A-3D, critical area increases in size with eccentricity.

FIGS. 4A and 4B shows the relation between various test stimuli and critical area at different locations (the nasal step region) for the same eccentricity. In each of FIGS. 4A-B, the vertical dashed line 400 represents the area tested by the Goldmann standard size III.

The vertical arrow 410 in FIG. 4A identifies the critical area when the stimulus is applied at an eccentricity of 10° and a nasal step of 165°. The vertical arrow 420 in FIG. 4B identifies the critical area when the stimulus is applied at an eccentricity of 10° and a nasal step of 195°.

As shown in FIGS. 4A-4B, critical area differs at different locations for the same eccentricity. Given the study of Redmond et al, the present inventors predicted that the 195° meridian, will on average display a larger loss that the 165° meridian resulting in a 'nasal step' sensitivity difference.

The present inventors have discovered that visual field loss in subjects having glaucoma and other ocular diseases affecting eccentricities outside the central ~5 degrees is equal across eccentricities if test stimuli are corrected for differences in spatial or temporal summation. Therefore, a global parameter such as the mean deviation (MD) that is calculated based upon the sensitivities derived by equating spatial summation location (i.e., all test stimuli within Ac following Ricco's law) will provide an early indicator of visual dysfunction. This discovery also predicts that significant differences between the upper and lower meridian identified by the global index (the Glaucoma Hemifield Test (GHT)) is an artifact due to comparing sensitivity values that are measured at different locations within the spatial summation continuum.

Table 3, hereinafter, shows test target sizes determined for different critical areas at various retinal eccentricities.

TABLE 3

|  | Ac | Ac (calculated) | Mean (Ac) | TEST size Criterion (1 log unit below Ac) | TEST size Criterion (0.75 log unit below Ac) | TEST size Criterion (0.5 log unit below Ac) |
|---|---|---|---|---|---|---|
| fovea | −1 |  | −1.00 | I | I | I |
| 5 deg | −0.75 | −1.1 | −0.93 | I | I | II |
| 10 deg | −0.75 | −0.89 | −0.82 | I or II | II | II |
| 15 deg | −0.5 | −0.75 | −0.63 | II | II | II |
| 20 deg (?) | −0.25 |  | −0.25 | II or III | II or III | III |

As can be seen in Table 3, three different criteria are used to set test size: 1, 0.75, and 0.5 log units below the critical area (Ac) at the different retinal eccentricities of: 0° (fovea), 5°, 10°, 15°, and 20°. This approach maximizes the possibility that early visual field loss will be identified at different eccentricities. In all cases, temporal summation is set at a level outside of complete summation (e.g., using a 200 ms test duration).

Figure 5:
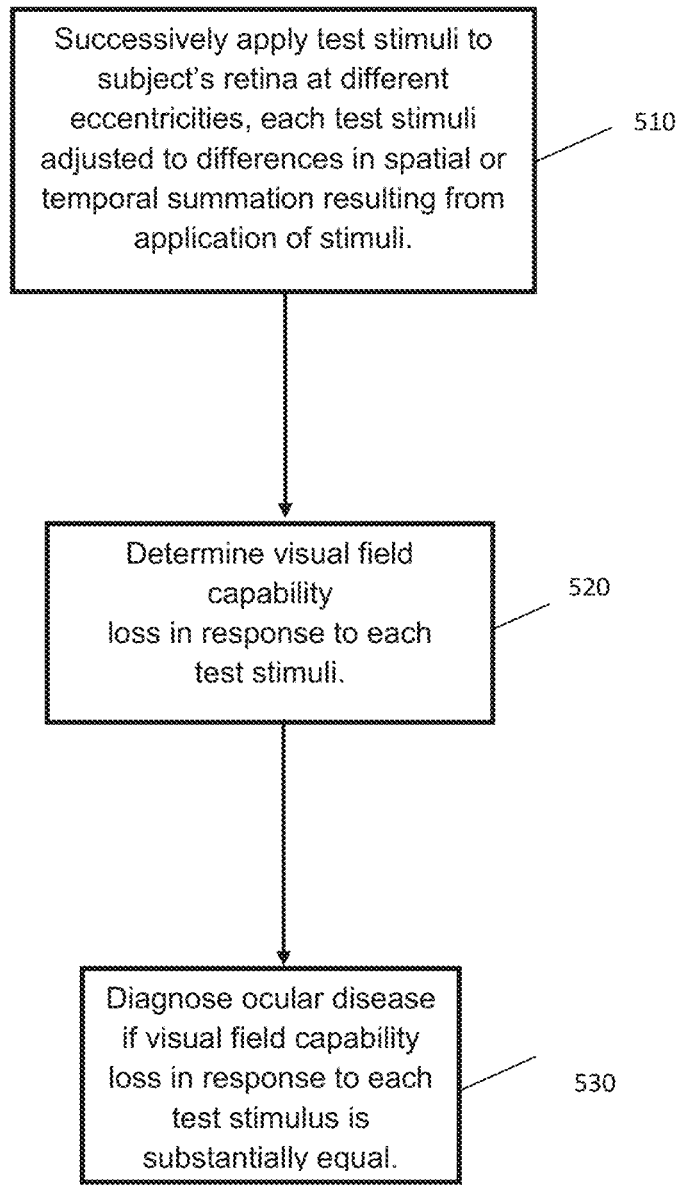
FIG. 5 is a flow diagram of a method for early detection of ocular disease in a subject in accordance with an embodiment of the present invention.

FIG. 5 is a flow diagram of a method for early detection of ocular diseases such as glaucoma in a subject. The method of FIG. 5 may, for example, be performed by modifying the software and/or firmware of commercially available Visual Field Analyzers such as the Humphrey® Field Analyzer HFA™ 11-i series, the Humphrey Matrix®, the Humphrey FDT® (all provided by Carl Zeiss Meditec), and the Octopus 900, 600 and 300 series Field Analyzers (all provided by Haag-Streit). Alternatively, the method of FIG. 5 may be performed by a general computer system adapted for visual field analysis such as the visual field analysis system 801 described hereinafter with reference to FIGS. 8A and 8B.

Referring to FIG. 5, a plurality of test stimuli are successively applied at different eccentricities to the subject's retina, at step 510. Each of the test stimuli is adjusted for differences in spatial or temporal summation resulting from application of the test stimuli. At step 520, visual field capability loss of the subject is determined in response to each of the plurality of test stimuli. Ocular disease, such as glaucoma is diagnosed in the subject at step 530 if the subject's visual field capability loss in response to each of the test stimuli is substantially equal.

The size of each of the test stimuli may, for example, be adjusted for differences in spatial summation. Further, the size of each of the test stimuli is preferably within Ricco's critical area (Ac). Each test stimulus may be of equal duration and preferably longer than Bloch's critical duration. The duration is preferably greater than 100 ms and is set at 200 ms in certain embodiments.

Visual field capability loss in a particular subject may, for example, be determined relative to subjects having normal visual field capability (i.e., visual field capability unaffected by ocular disease). Contrast threshold (and/or sensitivity) is typically constant within approximately the central 30 degrees of the visual field. Thus, providing a suitable test size (i.e., a large enough test size) is employed, sensitivity will generally be equal at all eccentricities for a subject having normal visual field capability. A cataract (not classed as an ocular disease), for example, would affect all thresholds. By employing smaller test sizes at various eccentricities, age-matched 'normative' data (i.e., data representative of a sample of subjects having normal visual field capability) can be generated. Visual field capability loss in a particular subject may then be determined by comparing contrast threshold (and/or sensitivity) data for the particular subject to the age-matched 'normative' data (at various eccentricities). Visual field loss may also be determined in other ways. For example, by comparing contrast threshold (and/or sensitivity) data for the particular subject at particular eccentricities to data at other eccentricities that may not be affected by the subject's visual field capability loss.

Figure 6:
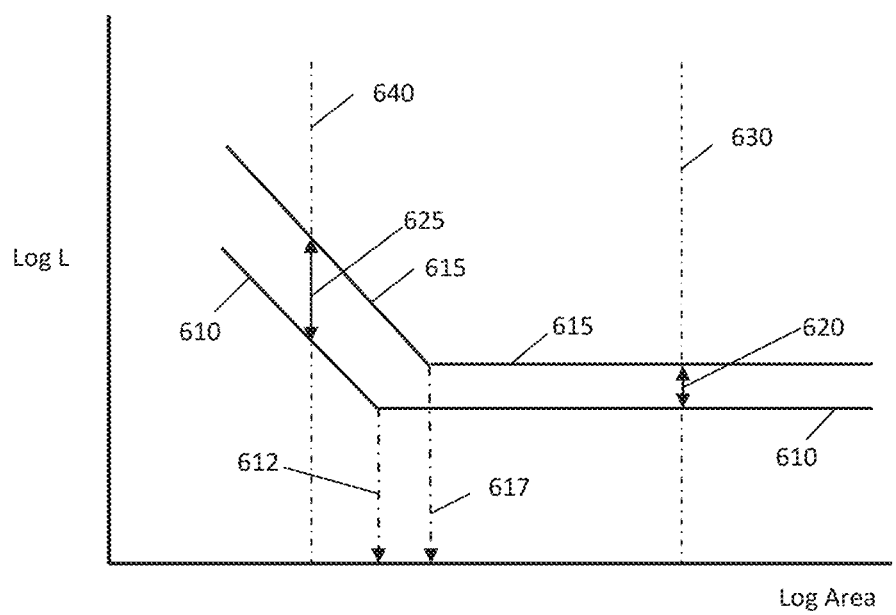
FIG. 6 is a graphical representation of threshold as a function of test stimulus area for subjects having normal visual field capability and subjects having visual field capability loss, respectively.

FIG. 6 comprises log-log plots of threshold as a function of area 610, 615 for subjects having normal visual field capability and subjects having visual field capability loss, respectively. Use of a large stimulus 630 (i.e., outside of Ricco's law (>Ac)) results in a visual field capability difference 620 between subjects having visual field capability loss 615 and subjects having normal visual field capability 610. This difference 620 is not due to ocular disease and could, for example, be due to cataract, uncorrected refractive error, age-related loss, etc. Use of a smaller stimulus 640 (i.e., within Ricco's law (<Ac)) results in a visual field capability difference 625 between subjects having visual field capability loss 615 and subjects having normal visual field capability 610. As can be seen from FIG. 6, the difference 625 is greater than the difference 620. This is because the visual field capability difference 625 comprises both the visual field capability difference 620 and the visual field capability loss detected in subjects having visual field capability loss 615 (the latter results from the stimulus being within Ricco's law (i.e., when the slope is −1)).

In accordance with another embodiment, a large stimulus and a small stimulus can be applied at multiple eccentricities (e.g., 6-10 locations) to measure sensitivities/thresholds. Any threshold elevation for the large stimuli would be due to non-disease factors such as cataract, uncorrected refractive error, age-related loss, etc. On the other hand, threshold changes for the stimuli for test targets within Ricco's law (i.e., small targets) will include both disease and non-disease factors.

In visual field nomenclature, the neutral density filter employed to attenuate the light is used to indicate threshold/sensitivity values. In order to compare test targets of various sizes, the present inventors defined a new decibel value denoted as 'dB*', which has been called the 'Cole-Harwerth' transformation. Given Ricco's law, where the multiple of test size and threshold are constant, dB* is defined as: dB*=dB (as per normal visual field output)+size factor. The size factor expressed in dB value for the different Goldmann sizes is as follows: size 0 (+18); size I (+12); size II (+6); size III (0); size IV (−6) and size V (−12). The sum of the dB output from a normal visual field output expressed in dB units, with the size correction, then provides a sensitivity value where the data points within Ricco's law are fitted with a line of zero slope. The dB* value within Ricco's law is the same irrespective of test size: the values beyond the critical area are not relevant as they reflect threshold/sensitivity values that are outside spatial summation (either within Piper's law or in the linear component). Using the dB* value, established decibel values are maintained when using size III target (done for ease of conversion), which advantageously enables comparison of thresholds within Ricco's law irrespective of test size.

Figure 7:
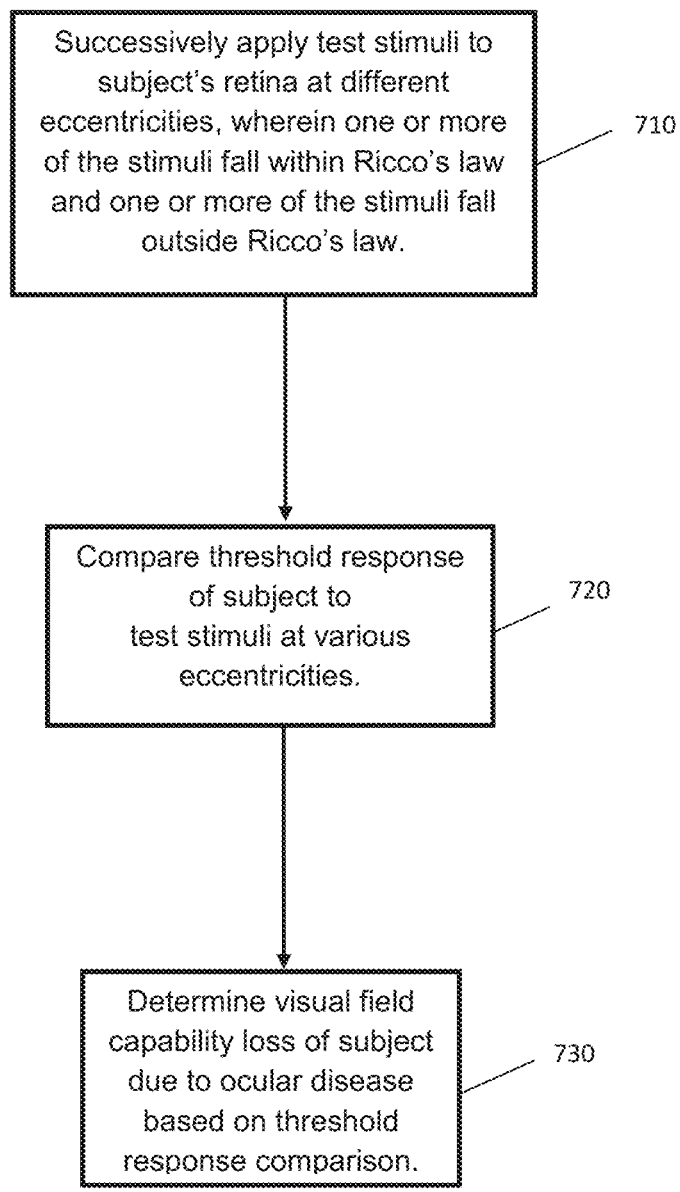
FIG. 7 is a flow diagram of a method for early detection of ocular disease in a subject in accordance with another embodiment of the present invention.

FIG. 7 is a flow diagram of a method for early detection of ocular diseases such as glaucoma in a subject. The method of FIG. 7 may, for example, be performed by modifying the software and/or firmware of commercially available Visual Field Analyzers such as the Humphrey® Field Analyzer HFA™ 11-i series, the Humphrey Matrix®, the Humphrey FDT® (all provided by Carl Zeiss Meditec), and the Octopus 900, 600 and 300 series Field Analyzers (all provided by Haag-Streit). Alternatively, the method of FIG. 7 may be performed by a general computer system adapted for visual field analysis such as the visual field analysis system 801 described hereinafter with reference to FIGS. 8A and 8B.

Referring to FIG. 7, a plurality of test stimuli are successively applied at different eccentricities to the subject's retina, at step 710. Certain of the test stimuli are of a size larger than the critical area (Ac), thus falling outside of Ricco's law (which corresponds to a slope of 0 on a log-log plot). Other of the test stimuli are of a size smaller than the critical area (Ac), thus falling within Ricco's law (which corresponds to a slope of −1 on a log-log plot). The threshold responses to each of the larger and smaller test stimuli are compared for different eccentricities at step 720. Based on the results of the threshold response comparison in step 720, visual field loss due to ocular disease is determined by differentiating from visual field loss due to a general reduction in sensitivity (e.g., resulting from cataract, uncorrected refractive error, age-related loss, etc.) at step 730.

Figure 8A:
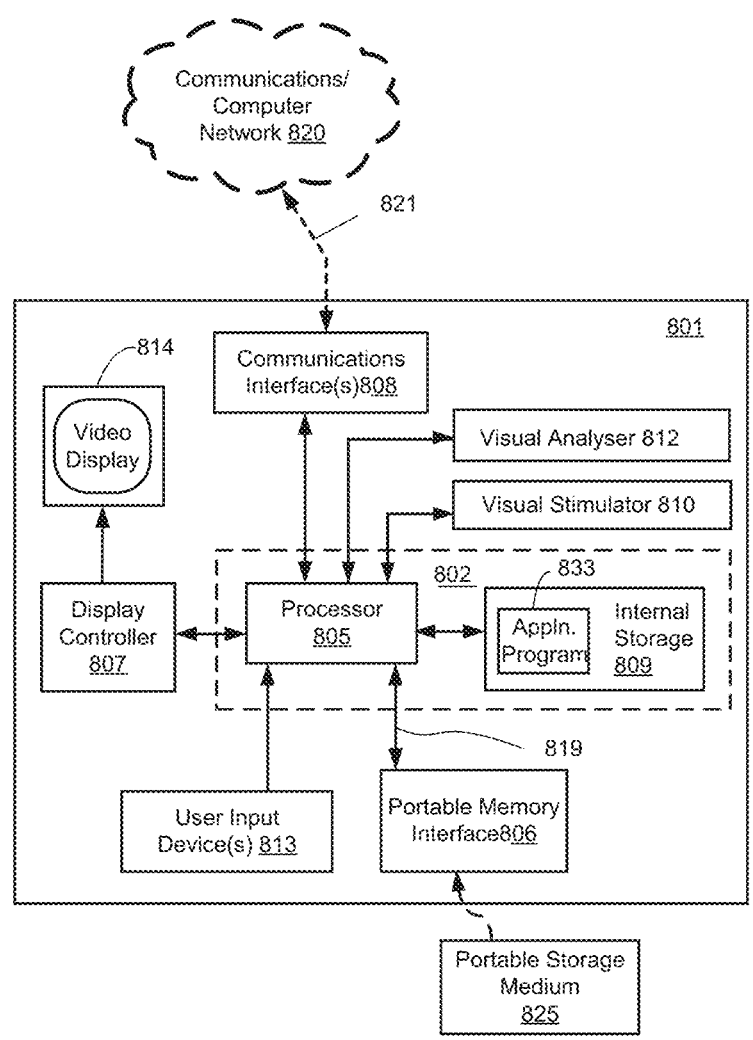
FIGS. 8A and 8B collectively comprise a block diagram of a visual field analysis system with which embodiments of the present invention can be practiced.
Figure 8B:
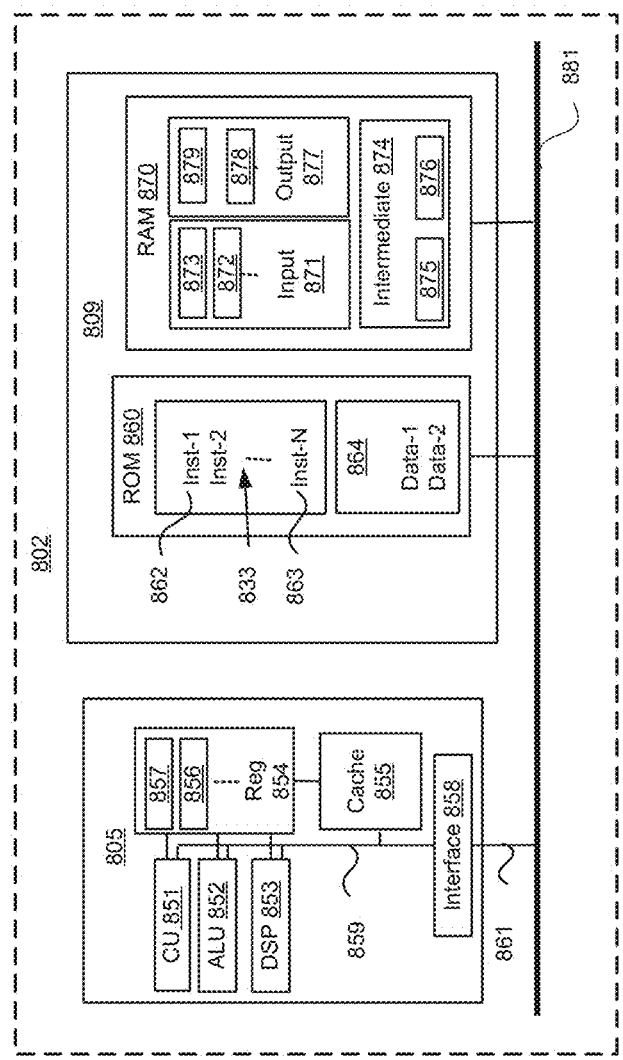

FIGS. 8A and 8B collectively form a schematic block diagram of a visual field analysis system 801 including embedded components, with which the methods described herein may be practiced. The visual field analysis system 801 may, for example, be a dedicated hardware platform, in which processing resources may be limited. Nevertheless, the methods described herein may also be performed on other general purpose systems such as desktop computers and server computers in conjunction with peripheral hardware.

As seen in FIG. 8A, the visual field analysis system 801 comprises an embedded controller 802. Accordingly, the visual field analysis system 801 may be referred to as an "embedded device." In the present example, the controller 802 has a processing unit (or processor) 805 which is bi-directionally coupled to an internal storage module 809. In certain embodiments, the processing unit 805 may comprise multiple processors. The storage module 809 may, for example, comprise non-volatile semiconductor read only memory (ROM) 860 and semiconductor random access memory (RAM) 870, as seen in FIG. 8B. The RAM 870 may be volatile, non-volatile or a combination of volatile and non-volatile memory.

The visual field analysis system 801 may include a display controller 807, which is connected to a video display 814, such as a liquid crystal display (LCD) panel or the like. The display controller 807 is configured for displaying graphical images on the video display 814 in accordance with instructions received from the embedded controller 802, to which the display controller 807 is connected.

The visual field analysis system 801 may also include user input devices 813 which are typically formed by keys, a keypad or like controls. In some implementations, the user input devices 813 may include a touch sensitive panel physically associated with the display 814 to collectively form a touch-screen. Such a touch-screen may thus operate as one form of graphical user interface (GUI) as opposed to a prompt or menu driven GUI typically used with keypad-display combinations. Other forms of user input devices may also be used, such as a microphone (not illustrated) for voice commands or a joystick/thumb wheel (not illustrated) for ease of navigation about menus.

As seen in FIG. 8A, the visual field analysis system 801 also comprises a portable memory interface 806, which is coupled to the processor 805 via a connection 819. The portable memory interface 806 allows a complementary portable memory device 825 to be coupled to the electronic device 801 to act as a source or destination of data or to supplement the internal storage module 809. Examples of such interfaces permit coupling with portable memory devices such as Universal Serial Bus (USB) memory devices, Secure Digital (SD) cards, Personal Computer Memory Card International Association (PCMIA) cards, optical disks and magnetic disks.

The visual field analysis system 801 also has a communications interface 808 to permit coupling of the visual field analysis system 801 to a computer or communications network 820 via a connection 821. The connection 821 may be wired or wireless. For example, the connection 821 may be radio frequency or optical. An example of a wired connection includes Ethernet. Further, an example of wireless connection includes Bluetooth™ type local interconnection, Wi-Fi (including protocols based on the standards of the IEEE 802.11 family), Infrared Data Association (IrDa) and the like.

The visual field analysis system 801 is configured to perform detection of ocular disease. The embedded controller 802, in conjunction with the visual stimulator 810 and the visual analyzer 812, is provided to detect ocular disease. The visual stimulator 810 and the visual analyzer 812 are both coupled to, and under the control of the embedded controller 802. In certain embodiments, the visual stimulator 810 may comprise an optical projector adapted to deliver test stimuli to a subject's retina. In other embodiments, test stimuli may be delivered to a subject's retina using the video display 814 or, alternatively, a second video display. In this case, the visual stimulator 810 may comprise a software module adapted to deliver test stimuli via a video display.

The methods described hereinbefore may be implemented using the embedded controller 802, where the processes of FIGS. 5 and 7 may be implemented as one or more software application programs 833 executable within the embedded controller 802. The visual field analysis system 801 of FIG. 8A implements the methods described herein. In particular, with reference to FIG. 8B, the steps of the described methods are effected by instructions in the software 833 that are carried out within the controller 802. The software instructions may be formed as one or more code modules, each for performing one or more particular tasks. The software may also be divided into two separate parts, in which a first part and the corresponding code modules performs the described methods and a second part and the corresponding code modules manage a user interface between the first part and the user.

The software 833 of the embedded controller 802 is typically stored in the non-volatile ROM 860 of the internal storage module 809. The software 833 stored in the ROM 860 can be updated when required from a computer readable medium. The software 833 can be loaded into and executed by the processor 805. In some instances, the processor 805 may execute software instructions that are located in RAM 870. Software instructions may be loaded into the RAM 870 by the processor 805 initiating a copy of one or more code modules from ROM 860 into RAM 870. Alternatively, the software instructions of one or more code modules may be pre-installed in a non-volatile region of RAM 870 by a manufacturer. After one or more code modules have been located in RAM 870, the processor 805 may execute software instructions of the one or more code modules.

The application program 833 is typically pre-installed and stored in the ROM 860 by a manufacturer, prior to distribution of the visual field analysis system 801. However, in certain instances, the application programs 833 may be supplied to the user encoded on one or more CD-ROM (not shown) and read via the portable memory interface 806 of FIG. 8A prior to storage in the internal storage module 809 or in the portable memory 825. In another alternative, the software application program 833 may be read by the processor 805 from the network 820, or loaded into the controller 802 or the portable storage medium 825 from other computer readable media. Computer readable storage media refers to any non-transitory tangible storage medium that participates in providing instructions and/or data to the controller 802 for execution and/or processing. Examples of such storage media include floppy disks, magnetic tape, CD-ROM, a hard disk drive, a ROM or integrated circuit, USB memory, a magneto-optical disk, flash memory, or a computer readable card such as a PCMCIA card and the like, whether or not such devices are internal or external of the visual field analysis system 801. Examples of transitory or non-tangible computer readable transmission media that may also participate in the provision of software, application programs, instructions and/or data to the visual field analysis system 801 include radio or infra-red transmission channels as well as a network connection to another computer or networked device, and the Internet or Intranets including e-mail transmissions and information recorded on Websites and the like. A computer readable medium having such software or computer program recorded on it is a computer program product.

The second part of the application programs 833 and the corresponding code modules mentioned above may be executed to implement one or more graphical user interfaces (GUIs) to be rendered or otherwise represented upon the display 814 of FIG. 8A. Through manipulation of the user input device 813 (e.g., the keypad), a user of the visual field analysis system 801 and the application programs 833 may manipulate the interface in a functionally adaptable manner to provide controlling commands and/or input to the applications associated with the GUI(s). Other forms of functionally adaptable user interfaces may also be implemented, such as an audio interface utilizing speech prompts output via loudspeakers (not illustrated) and user voice commands input via the microphone (not illustrated).

FIG. 8B illustrates in detail the embedded controller 802 having the processor 805 for executing the application programs 833 and the internal storage 809. The internal storage 809 comprises read only memory (ROM) 860 and random access memory (RAM) 870. The processor 805 is able to execute the application programs 833 stored in one or both of the connected memories 860 and 870. When the visual field analysis system 801 is initially powered up, a system program resident in the ROM 860 is executed. The application program 833 permanently stored in the ROM 860 is sometimes referred to as "firmware". Execution of the firmware by the processor 805 may fulfill various functions, including processor management, memory management, device management, storage management and user interface.

The processor 805 typically includes a number of functional modules including a control unit (CU) 851, an arithmetic logic unit (ALU) 852 and a local or internal memory comprising a set of registers 854 which typically contain atomic data elements 856, 857, along with internal buffer or cache memory 855. One or more internal buses 859 interconnect these functional modules. The processor 805 typically also has one or more interfaces 858 for communicating with external devices via system bus 881, using a connection 861.

The application program 833 includes a sequence of instructions 862 through 863 that may include conditional branch and loop instructions. The program 833 may also include data, which is used in execution of the program 833. This data may be stored as part of the instruction or in a separate location 864 within the ROM 860 or RAM 870.

In general, the processor 805 is given a set of instructions, which are executed therein. This set of instructions may be organized into blocks, which perform specific tasks or handle specific events that occur in the visual field analysis system 801. Typically, the application program 833 waits for events and subsequently executes the block of code associated with that event. Events may be triggered in response to input from a user, via the user input devices 813 of FIG. 8A, as detected by the processor 805. Events may also be triggered in response to other sensors and interfaces in the visual field analysis system 801.

The execution of a set of the instructions may require numeric variables to be read and modified. Such numeric variables are stored in the RAM 870. The disclosed method uses input variables 871 that are stored in known locations 872, 873 in the memory 870. The input variables 871 are processed to produce output variables 877 that are stored in known locations 878, 879 in the memory 870. Intermediate variables 874 may be stored in additional memory locations in locations 875, 876 of the memory 870. Alternatively, some intermediate variables may only exist in the registers 854 of the processor 805.

The execution of a sequence of instructions is achieved in the processor 805 by repeated application of a fetch-execute cycle. The control unit 851 of the processor 805 maintains a register called the program counter, which contains the address in ROM 860 or RAM 870 of the next instruction to be executed. At the start of the fetch execute cycle, the contents of the memory address indexed by the program counter is loaded into the control unit 851. The instruction thus loaded controls the subsequent operation of the processor 805, causing for example, data to be loaded from ROM memory 860 into processor registers 854, the contents of a register to be arithmetically combined with the contents of another register, the contents of a register to be written to the location stored in another register and so on. At the end of the fetch execute cycle the program counter is updated to point to the next instruction in the system program code. Depending on the instruction just executed this may involve incrementing the address contained in the program counter or loading the program counter with a new address in order to achieve a branch operation.

Each step or sub-process in the processes of the methods described below is associated with one or more segments of the application program 833, and is performed by repeated execution of a fetch-execute cycle in the processor 805 or similar programmatic operation of other independent processor blocks in the visual field analysis system 801.

Existing methods and systems use test stimuli that are of one size and one test duration at all retinal eccentricities and/or locations. Embodiments of the present invention, on the other hand, advantageously adjust test stimuli such that visual function can be determined at all retinal eccentricities under equivalent conditions.

The foregoing detailed description provides exemplary embodiments only, and is not intended to limit the scope, applicability or configurations of the invention. Rather, the description of the exemplary embodiments provides those skilled in the art with enabling descriptions for implementing an embodiment of the invention. Various changes may be made in the function and arrangement of elements without departing from the spirit and scope of the invention as set forth in the claims hereinafter.

(Australia Only) In the context of this specification, the word "comprising" means "including principally but not necessarily solely" or "having" or "including", and not "consisting only of". Variations of the word "comprising", such as "comprise" and "comprises" have correspondingly varied meanings.

The invention claimed is:

1. A method for early detection of ocular disease in a subject, the method comprising:
    causing, by one or more processors of a visual field analysis system, application of a first test stimuli at a first eccentricity to a retina of the subject;
    determining, by the one or more processors, a difference in at least one of a spatial summation or a temporal summation from a first response to the first test stimuli;
    causing, by the one or more processors, application of a second test stimuli different than the first test stimuli, the second test stimuli applied at a second eccentricity to the retina, wherein a size of the second test stimuli is adjusted for the determined difference in the at least one of the spatial summation or the temporal summation resulting from application of the first test stimuli to the retina of the subject, wherein a size of the first test stimuli and the size of the second test stimuli are within Ricco's critical area (Ac);
    performing a first comparison, by the one or more processors, of the first response to a first threshold;
    performing a second comparison, by the one or more processors, of a second response to the second test stimuli to a second threshold;
    determining, by the one or more processors, a first visual field capability loss of said subject based on the first comparison;
    determining, by the one or more processors, a second visual field capability loss of said subject based on the second comparison; and
    diagnosing, by the one or more processors, ocular disease in said subject if said first visual field capability loss and said second visual field capability loss is substantially equal.

2. The method of claim 1, wherein the size of the second test stimuli is adjusted for differences in spatial summation.

3. The method of claim 2, wherein the first test stimuli and the second test stimuli are of equal duration.

4. The method of claim 1, wherein durations of the first test stimuli and the second test stimuli are longer than Bloch's critical duration.

5. The method of claim 4, wherein durations of the first test stimuli and the second test stimuli are greater than 100 ms.

6. The method of claim 4, wherein durations of the first test stimuli and the second test stimuli are 200 ms.

7. A visual field analyzer comprising:
    a machine readable medium including machine executable instructions; and
    one or more processors to execute the instructions to perform the method of claim 1.

8. The method of claim 1, wherein determining at least one of the first visual field capability loss or the second visual field capability loss includes using a mean deviation calculated based upon sensitivities derived by equating spatial summation location.

9. A visual field analysis system comprising:
    at least one processor;
    a memory to store program instructions and data;
    a visual stimulator to deliver visual stimuli to a subject's retina;
    a visual analyzer to determine visual field capability loss in said subject; and
    a video display to output data;
    wherein said at least one processor is to execute the instructions to:
        activate said visual stimulator to deliver a first test stimuli at a first eccentricity to the subject's retina;
        determine a difference in at least one of spatial summation or temporal summation from a first response to the first test stimuli;
        activate said visual stimulator to deliver a second test stimuli different than the first test stimuli, the second test stimuli delivered at a second eccentricity to the retina, wherein a size of the second test stimuli is adjusted for the determined difference in at least one of a spatial summation or a temporal summation resulting from the delivery of the first test stimuli to the retina of the subject, wherein a size of the first test stimuli and the size of the second test stimuli are within Ricco's critical area (Ac);
        perform a first comparison of the first response to a first threshold;
        perform a second comparison of a second response to the second test stimuli to a second threshold;
        activate said visual analyzer to identify a first visual field capability loss of said subject based on the first comparison;
        activate said visual analyzer to identify a second visual field capability loss of said subject based on the second comparison;
        determine whether the first visual field capability loss and the second visual field capability loss are substantially equal; and
        activate said video display to output a result of said determination.

10. The visual field analysis system of claim 9, wherein the size of the second test stimuli is adjusted for differences in spatial summation.

11. The visual field analysis system of claim 10, wherein the first test stimuli and the second test stimuli are of equal duration.

12. The visual field analysis system of claim 9, wherein durations of the first test stimuli and the second test stimuli are longer than Bloch's critical duration.

13. The visual field analysis system of claim 12, wherein durations of the first test stimuli and the second test stimuli are greater than 100 ms.

14. The visual field analysis system of claim 13, wherein durations of the first test stimuli and the second test stimuli are 200 ms.

15. The visual field analysis system of claim 9, wherein the at least one processor is to determine at least one of the first visual field capability loss or the second visual field capability loss by using a mean deviation calculated based upon sensitivities derived by equating spatial summation location.

* * * * *